US011307113B2

United States Patent
Hofmann et al.

(10) Patent No.: US 11,307,113 B2
(45) Date of Patent: Apr. 19, 2022

(54) METHOD AND DEVICE FOR DETERMINING THE STATUS OF PASSIVATION LAYERS OF AN ENCAPSULATION

(71) Applicants: AESCULAP AG, Tuttlingen (DE); EBERHARD KARLS UNIVERSITÄT TÜBINGEN, Tübingen (DE)

(72) Inventors: Boris Hofmann, Balgheim (DE); Markus Westerhausen, Reutlingen (DE)

(73) Assignees: AESCULAP AG, Tuttlingen (DE); EBERHARD KARLS UNIVERSITÄT TÜBINGEN, Tubingen (DE)

( * ) Notice: Subject to any disclaimer, the term of this patent is extended or adjusted under 35 U.S.C. 154(b) by 96 days.

(21) Appl. No.: 16/638,960

(22) PCT Filed: Aug. 16, 2018

(86) PCT No.: PCT/EP2018/072265
§ 371 (c)(1),
(2) Date: Feb. 13, 2020

(87) PCT Pub. No.: WO2019/034749
PCT Pub. Date: Feb. 21, 2019

(65) Prior Publication Data
US 2020/0191681 A1 Jun. 18, 2020

(30) Foreign Application Priority Data
Aug. 16, 2017 (DE) .......................... 102017118686.7

(51) Int. Cl.
*G01M 3/16* (2006.01)

(52) U.S. Cl.
CPC .......... *G01M 3/16* (2013.01); *A61B 2562/125* (2013.01)

(58) Field of Classification Search
CPC .......................... G01M 3/16; A61B 2562/125
See application file for complete search history.

(56) References Cited

U.S. PATENT DOCUMENTS

| 4,677,373 A | 6/1987 | Kobayashi et al. | |
| 5,223,458 A * | 6/1993 | Shanfield | H01L 21/022 438/761 |

(Continued)

FOREIGN PATENT DOCUMENTS

| DE | 3623872 A1 | 1/1987 |
| DE | 4341118 A1 | 6/1995 |

(Continued)

OTHER PUBLICATIONS

German Search Report for German Application No. 10 2017 118 686.7, dated Oct. 23, 2017, 11 pages.

(Continued)

*Primary Examiner* — Alexander Satanovsky
*Assistant Examiner* — Lynda Dinh
(74) *Attorney, Agent, or Firm* — Culhane Meadows, PLLC; Christopher A. Rothe

(57) ABSTRACT

A method is used for determining a status of an encapsulation and/or a passivation layer of the encapsulation. The encapsulation forms a multi-layer system from multiple passivation layers arranged on top of one another and electrically contacted intermediate layers arranged between the passivation layers. The multi-layer system protects an implant surrounded by the encapsulation. In the method, an electrical measurement is carried out between a reference potential and at least one electrically contacted intermediate layer, and at least one current flowing between the reference (Continued)

Figure 1:
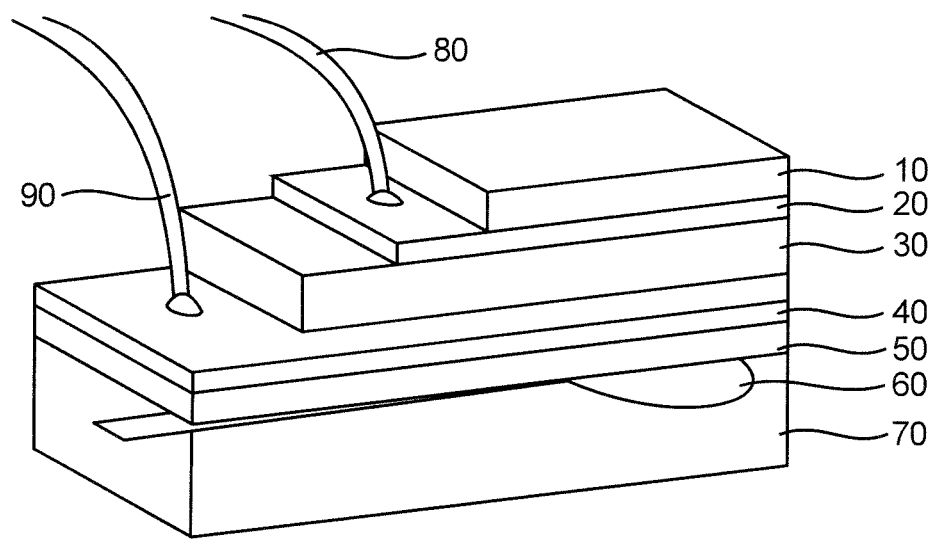

potential and the at least one electrically contacted intermediate layer is detected. The at least one detected current is compared with at least one pre-determined threshold value. If the detected current falls below or exceeds the at least one threshold value, this indicates a functional state of a passivation layer adjacent to the at least one electrically contacted intermediate layer.

8 Claims, 4 Drawing Sheets

(56) References Cited

U.S. PATENT DOCUMENTS

| | | | |
|---|---|---|---|
| 5,750,926 | A | 5/1998 | Schulman et al. |
| 9,570,662 | B2 * | 2/2017 | Taeger ................ H01L 33/56 |
| 10,132,843 | B2 * | 11/2018 | Krainer ................ H02M 1/00 |
| 10,918,298 | B2 * | 2/2021 | Rogers ................ H05K 1/0283 |
| 2002/0022016 | A1 * | 2/2002 | Walsh ................ A61K 9/1694 |
| | | | 424/93.1 |
| 2002/0042561 | A1 | 4/2002 | Schulman et al. |
| 2003/0181953 | A1 | 9/2003 | Dropps et al. |
| 2005/0159800 | A1 | 7/2005 | Marshall et al. |
| 2009/0308762 | A1 | 12/2009 | Tiedtke |
| 2013/0126999 | A1 * | 5/2013 | Rusian ................ H01L 31/085 |
| | | | 257/428 |
| 2018/0235544 | A1 * | 8/2018 | Nagarkar ............... B33Y 80/00 |

FOREIGN PATENT DOCUMENTS

| | | |
|---|---|---|
| DE | 10036362 A1 | 1/2002 |
| DE | 102004052801 A1 | 5/2006 |
| DE | 102008039857 A1 | 4/2010 |
| DE | 102010018039 A1 | 11/2010 |
| EP | 0278503 A2 | 8/1988 |

OTHER PUBLICATIONS

International Search Report and Written Opinion for International Application PCT/EP2018/072265, dated Oct. 11, 2018, 11 pages.

* cited by examiner

METHOD AND DEVICE FOR DETERMINING THE STATUS OF PASSIVATION LAYERS OF AN ENCAPSULATION

CROSS REFERENCE TO RELATED APPLICATIONS

This application is the United States national phase entry of International Application No. PCT/EP2018/072265, filed Aug. 16, 2018, which claims the benefit of priority of German Application No. 10 2017 118 686.7, filed Aug. 16, 2017. The contents of International Application No. PCT/EP2018/072265 and German Application No. 10 2017 118 686.7 are incorporated by reference herein in their entireties.

FIELD

The invention relates to a method for determining a status of encapsulations and/or passivation layers and especially refers to a method for electrical measurement on conducting intermediate layers interposed between passivation layers of an encapsulation and the analysis thereof with respect to a functional state of a passivation layer.

BACKGROUND

For therapeutic and diagnostic methods, electrically active and/or flexible implants are known, for example. The encapsulation of such flexible implants must be biostable, biocompatible and electrically insulating.

Common polymers such as polyimide or parylene (poly-p-xylylene) ensure at least said properties, but they are permeable to steam in small quantities and therefore are not completely diffusion-tight. Over a quite long period of time this results in several degradation effects on the implant.

By embedding steam-impermeable layers and, resp., intermediate layers in passivation layers or reducing delamination of insulating layers of interposed steam-impermeable layers by specific adhesion layers which increase adhesion to other materials, the long-term stability of the flexible encapsulation and thus of the flexible implant can be improved, to be sure.

However, so far it has not been possible to carry out in-vivo monitoring of the passivation and to make a (real time) statement about the status of the flexible encapsulations. Encapsulations and, resp., implants at present can be determined merely as either being still functional and thus insulating or as being defective and thus, in the worst case, separated from electrically active layers. Progressive ageing of the passivation which has not been observable so far usually results in sudden and thus undesired failure of the implant without any determinable detectability by e.g. readable signaling.

SUMMARY

Against this background, an object underlying the invention is to provide a method for determining the status of passivation layers of an encapsulation by which degradation effects on flexible passivating layers can be determined at an early stage.

The invention is based on the general idea to detect, by an electrical analysis and/or electrical measurements and subsequent assessment of (individual) passive layers by means of introduced intermediate layers, negative degradation effects within said passivation at an early stage. For example, electrical contacting of intermediate layers made from conductive material in a passivating multi-layer system with an object to be protected, for example a flexible implant, or with flexible or non-flexible polyimide layers including interposed structures made from conductive material can permit the analysis of at least one passivating layer. This can be done already in advance for defining/checking production rejects, but also permits real-time monitoring with regard to material fatigue, especially while the implant is already dwelling in vivo in the body. Thus, advantageously a deterioration of the passivating properties of individual layers can be detected in advance, while the entire system as such is still stable, and in vivo failure/health analysis of a (still functioning) implant passivation as well as detection of production reject become possible without the aid of external references.

In other words, it is suggested according to the invention to continuously monitor the individual passivation layers via current measurement for impairment, i.e. deterioration of their properties, at a predetermined starting time and then in a status of use. Selectively applying an electric signal, for example a voltage of predetermined value (e.g. IV), to the contacts of the intermediate layers and/or at least one electrode and, resp., one determining point of the object to be protected, preferably implant, against a reference component or a reference potential (extra-system at the starting time or intra-system in vivo and, resp., during use) permits selective measurement on each passivation layer and thus providing information on whether any impairment of a passivation layer is given and if so, which of the passivation layers is impaired. Since a period of time over which for example a top passivation layer loses its passivating property is known or can be determined at least empirically by approximation (e.g. 60.5 days in the example underlying here), a point in time of system-relevant failure of individual passivation layers or else of the overall system or, resp., implant can be predicted or estimated at least by approximation. Moreover, the initial measurement at the end of the manufacturing process enables those systems for which premature failure can be detected as probable to be sorted out already before use thereof.

In detail, a method for determining a status of an encapsulation and/or a passivation layer of the encapsulation, wherein the encapsulation forms a multi-layer system from multiple passivation layers alternated on top of one another and electrically contacted intermediate layers interposed between the passivation layers, the multi-layer system is arranged to protect an object surrounded by the encapsulation, preferably an implant, and a top layer and a bottom layer of the multi-layer system are formed each by a respective top passivation layer and a respective bottom passivation layer, comprises the steps of: carrying out an electrical measurement using an electrical signal between a reference potential and at least one electrically contacted intermediate layer, and detecting at least one current flowing between the reference potential and the at least one electrically contacted intermediate layer; and comparing the at least one detected current with at least one predetermined threshold value, wherein, if the current falls below or exceeds the at least one threshold value, this indicates a functional state of a passivation layer adjacent to the at least one electrically contacted intermediate layer. An electrical measurement in this context is understood to be, for example, DC signal measurements using an electrical DC signal or AC signal measurements using an AC signal.

Of preference, in the afore-mentioned method plural electrically contacted intermediate layers which are interposed between two respective passivation layers of the encapsulation are measured against a common reference potential; for each of the plural intermediate layers a measuring current is detected which is assigned to a corresponding one of the passivation layers and indicates the functional state thereof; and each measuring current is compared to a respective predetermined threshold value, wherein exceeding of the predetermined threshold value indicates an impaired state of the respective assigned passivation layer. Accordingly, the common reference potential may also be one of the intermediate layers themselves or can be formed by the latter. A common potential can be applied externally with the help of the reference electrode and can then be tapped via the intermediate layers, or can be applied internally with the help of the intermediate layers themselves. For example, a potential may be applied at an upper intermediate layer and said potential can be tapped via a central intermediate layer, or else a potential may be applied e.g. at a lower intermediate layer and said potential can be tapped via the central intermediate layer.

Of preference, the predetermined threshold value is zero and a comparison of detected measuring currents over plural layer sequences indicates an overall status of the multi-layer system forming the encapsulation, wherein, when the comparison indicates that at least between a detecting point of the object to the protected, preferably implant, and an intermediate layer separated therefrom by the bottom passivation layer no measuring current is detectable, functional stability of the overall system is concluded irrespective of a determined status of higher passivation layers.

Of preference, the predetermined threshold value is zero and a comparison of detected measuring currents over plural layer sequences indicates an overall status of the multi-layer system forming the encapsulation, wherein, when the multi-layer system includes at least one upper, one central and one lower passivation layer, and when in an initial system check measurement after the end of production of the overall system a measurable current is detected between a first intermediate layer arranged between the upper and central passivation layers and a second intermediate layer arranged between the central and the lower passivation layers via the central passivation layer, a basic impairment of at least the central passivation layer and/or of the overall system which involves reject is concluded.

Of preference, in the afore-described method the encapsulation is arranged to encapsulate an implant, preferably a flexible implant, as the object to be protected, preferably implant, in vivo in a fluid-tight and/or gas-tight manner, and the method is configured to carry out, by way of analysis and assessment of at least one passivating layer by electrical measurement, an in vivo failure analysis and/or health analysis of the implant passivation and/or detection of production reject while external reference components are omitted.

Of preference, the electrical measurement is carried out free from external reference between two electrically contacted intermediate layers. For the electrical measurement preferably via the intermediate layers themselves, a potential is applied to a first intermediate layer and tapping is effectuated on a second intermediate layer. In a subsequent measurement, i.e. a new measurement with a new potential, the new potential is then applied to the second intermediate layer, for example, and tapping is effectuated on a third intermediate layer. By means of electrical measurements following such sequence corresponding to the number of given intermediate layers, advantageously a production reject becomes apparent and a classification or, resp., judgment of the individual passivation layers in terms of quality becomes possible.

Of preference, the electrical measurement is carried out on a biostable, biocompatible and electrically insulating encapsulation.

Of preference, in the afore-mentioned method the steps thereof are carried out for pre-detecting an impairment of passivating properties on an overall system that is still passivated in a stable manner.

Furthermore, the invention relates to a determining device for determining a status of an encapsulation and/or a passivation layer of the encapsulation, wherein the encapsulation forms a multi-layer system from multiple alternately superimposed passivation layers and electrically contacted intermediate layers interposed between the passivation layers, the multi-layer system is arranged to protect an implant surrounded by the encapsulation, and a top layer and a bottom layer of the multi-layer system are formed by a respective top and a respective bottom passivation layer, wherein a measuring device is configured and provided for carrying out an electrical measurement between a reference potential and at least one electrically contacted intermediate layer and for detecting at least one current flowing between the reference potential and the at least one electrically contacted intermediate layer and a comparing unit is configured and provided for comparing the at least one detected current with at least one predetermined threshold value, wherein, if the detected current falls below or exceeds the at least one threshold value, this indicates a functional state of a passivation layer adjacent to the at least one electrically contacted intermediate layer.

BRIEF DESCRIPTION OF THE DRAWING FIGURES

Figure 2:
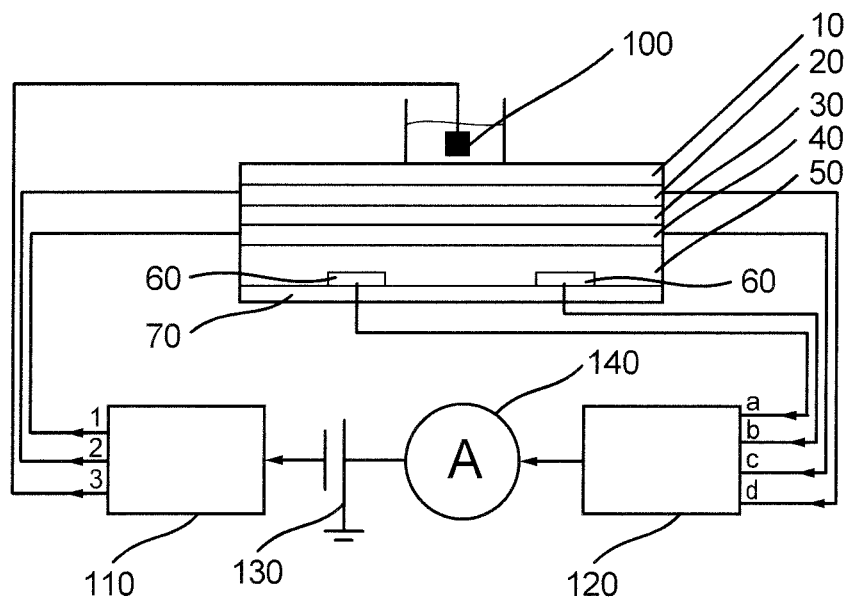
Figure 3:
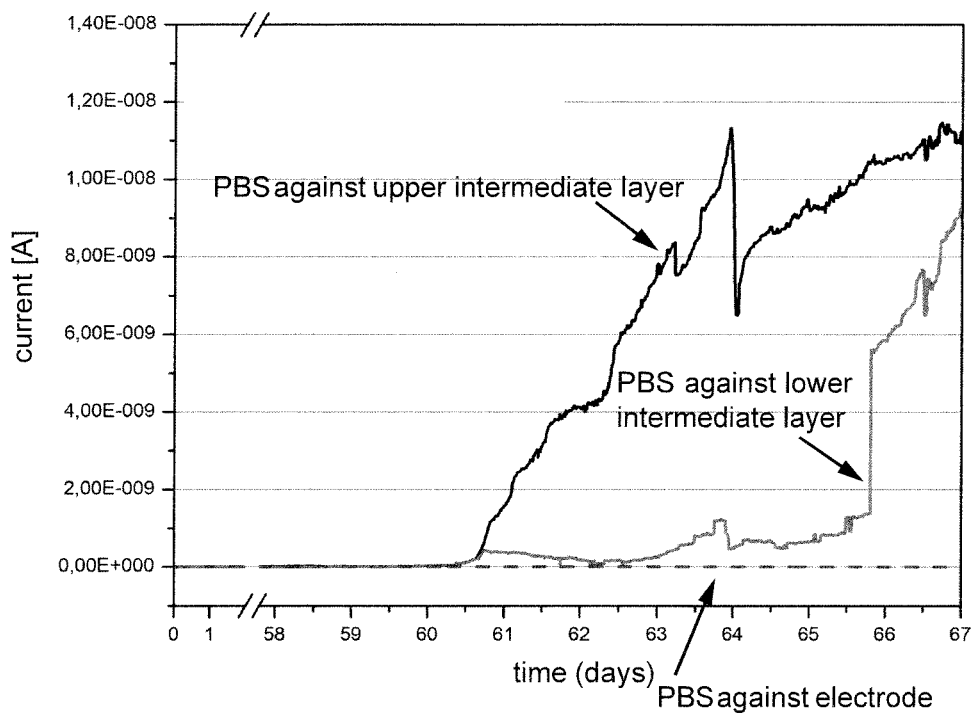
Figure 4:
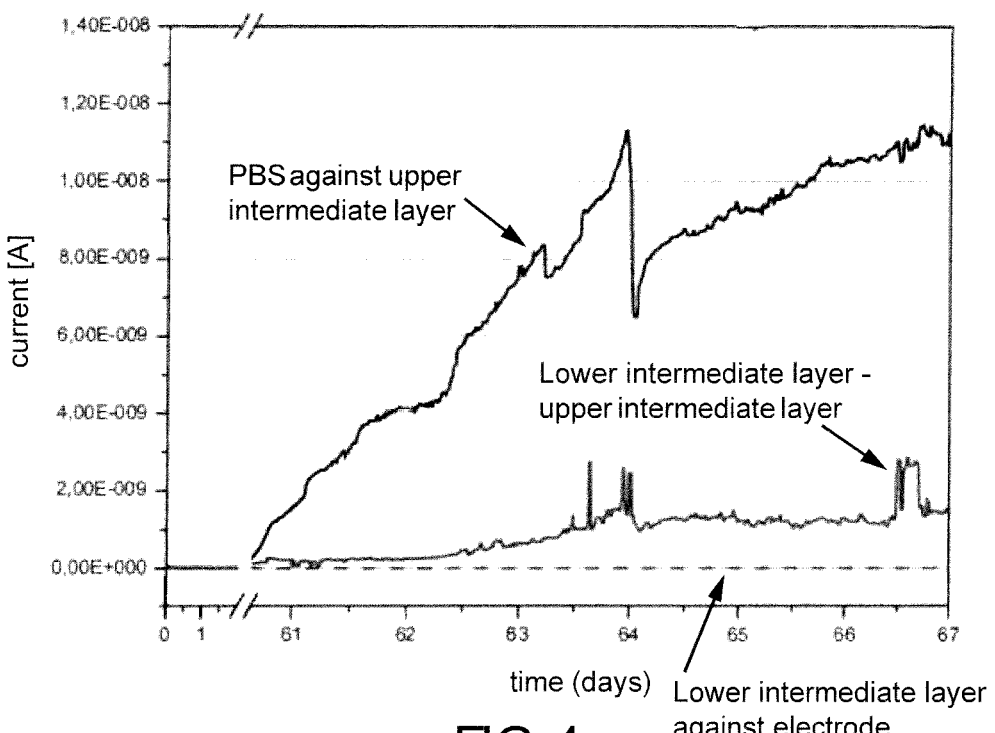
Figure 5:
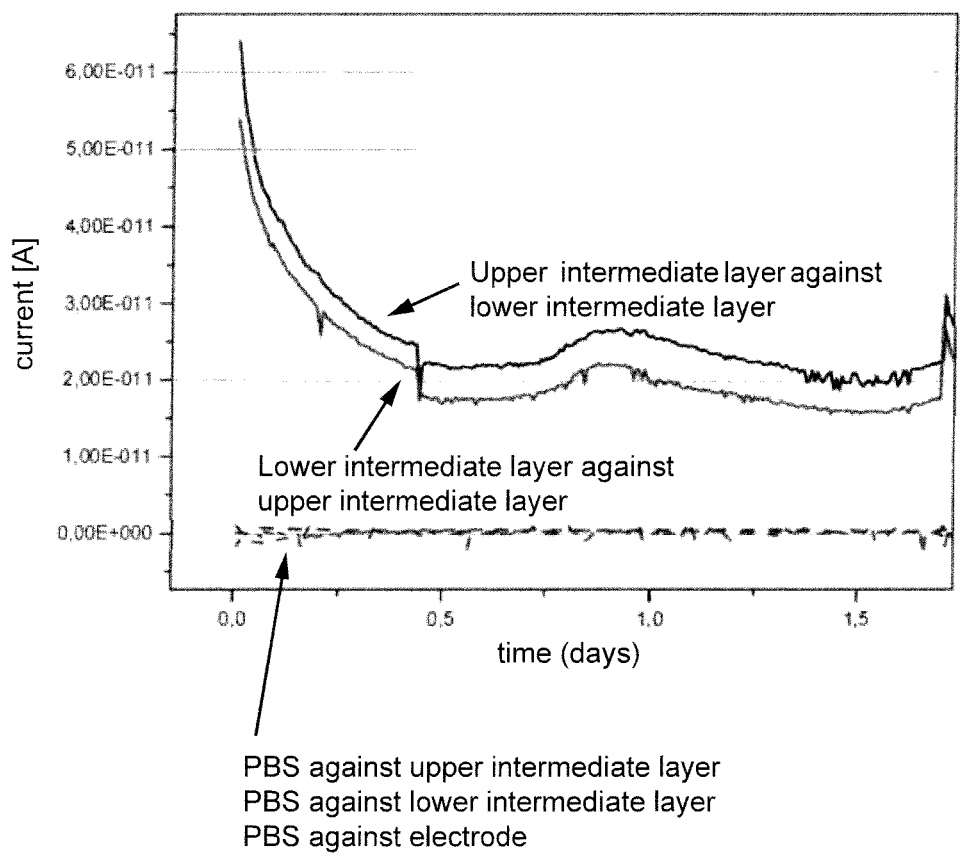
Figure 6:
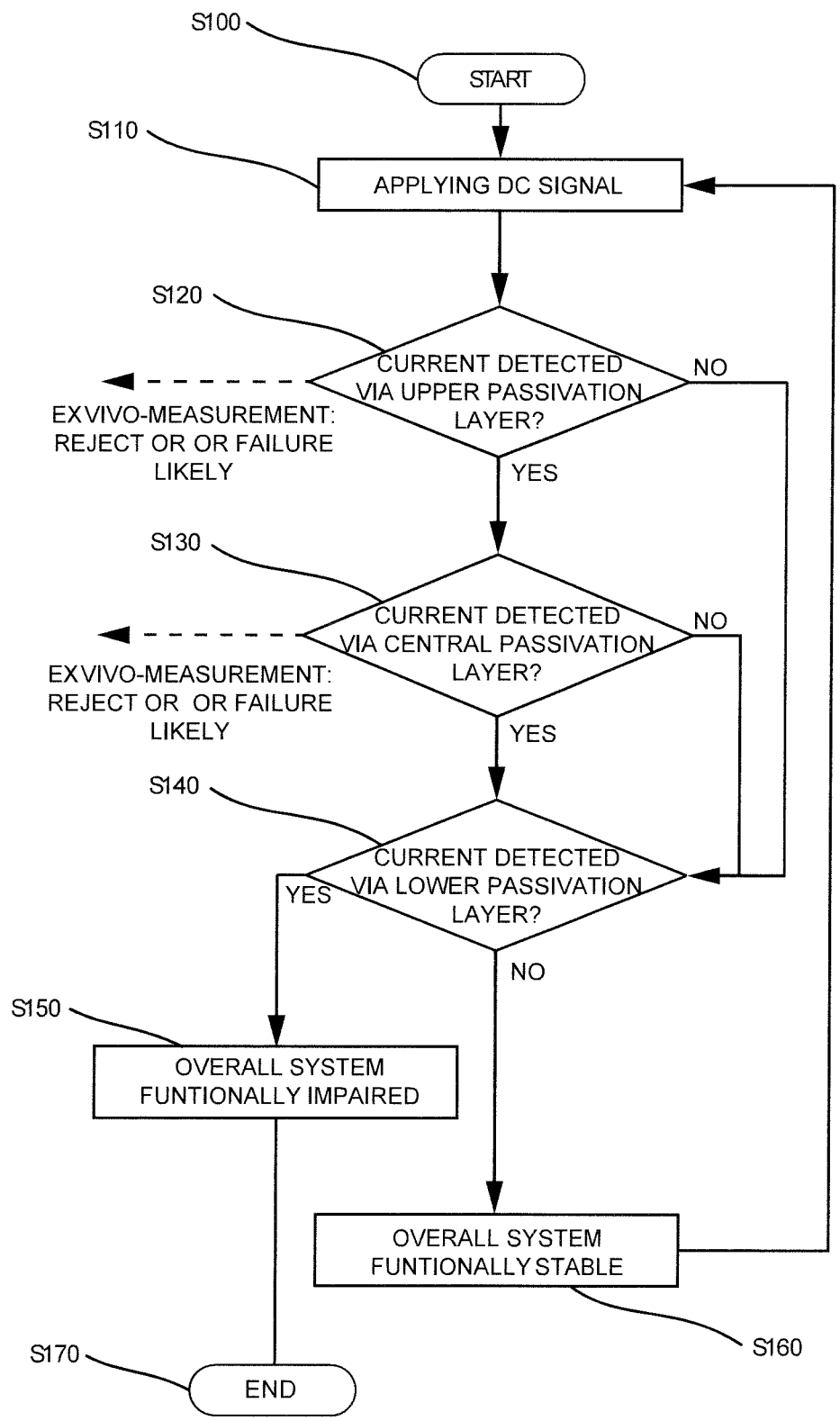

In the following, the invention will be described in detail with further advantages and effects by way of preferred example embodiments with reference to the drawing, wherein:

FIG. 1 schematically and partially shows a multi-layer passivation system for e.g. an implant having electrical access to two electrically contacted intermediate layers in the passivation via an electrode;

FIG. 2 schematically shows a principle of the measurement on passivating layers of the passivation system of FIG. 1;

FIG. 3 schematically shows measuring signal sequences of electrical measurements (DC signal measurements: reference/PBS—upper intermediate layer, reference/PBS—lower intermediate layer, reference/PBS—implant electrode) on the implant of FIG. 1;

FIG. 4 schematically shows measuring signal sequences of electrical measurements (DC signal measurements: reference/PBS—upper intermediate layer, lower intermediate layer—upper intermediate layer, lower intermediate layer—implant electrode) on the implant of FIG. 1;

FIG. 5 schematically shows measuring signal sequences of electrical measurements (DC signal measurements: upper intermediate layer—lower intermediate layer, lower intermediate layer—upper intermediate layer, as well as reference/PBS against the respective upper intermediate layer, the lower intermediate layer and the implant electrode) on the implant of FIG. 1 especially for the detection of production rejects; and FIG. 6 in extracts and simplified shows a flow diagram of a method for determining the status of passivation layers according to one example configuration.

Like or functionally equivalent features are provided with like reference numerals in the individual figures and appropriately are not redundantly described. Figures need not necessarily be considered to be true to scale. There is no restriction to measuring units given in the figures.

DETAILED DESCRIPTION

FIG. 1 schematically illustrates, for a structure of a one-sided passivation, an electrical access to two intermediate layers in a passivation above an electrode in a multi-layer system for a flexible implant.

In FIG. 1, the reference numeral 10 denotes an upper or first passivation layer, the reference numeral 20 denotes a first intermediate layer produced from a conductive material, the reference numeral 30 denotes a central or second passivation layer, the reference numeral 40 denotes a second intermediate layer equally produced from a conductive material, the reference numeral 50 denotes a lower or third passivation layer and the reference numeral 60 denotes a (schematically indicated) electrode or a detection point of an implant which is protected by the passivating multi-layer system 10, 30, 50. In other words, the passivation schematically indicated in FIG. 1 protects the implant, indicated by way of example by the electrode 60, from versatile negative degradation effects. The reference 70 indicates, by way of example, a type of substrate or a part of the implant, for example.

Here "by way of example" means that an implant need not necessarily include in fact an "electrode" in the actual sense but that such term may be helpful to describe correlations. Whereas, practically preferred, the electrical measurement is carried out between (e.g. two) intermediate layers, in the exemplary system shown here an electrode may be diverted from its intended use for this purpose. In the substrate used according to the example embodiment, the electrode was diverted for the measurement, for example. A conductive material here is understood to be a metal, a conductive semiconductor or generally an electrically conductive material or an appropriate material, for example.

Electrical contacts 80, 90 with each of the first intermediate layer 20 and the second intermediate layer 40, also referred to as bottom layer (at the bottom) and, resp., top layer (at the top), permit an analysis of a respective passivating layer, for example a polyimide layer.

FIG. 2 schematically illustrates a principle of the measurement on passivating layers of the passivating system of FIG. 1. This means that usually the functional property of passivation is tested by means of a reference electrode 100 put in an electrically active and, resp., conducting liquid above the implant, as shown in FIG. 2. Impedance measurements vis-à-vis passivated components, in this case the multi-layer system or parts thereof, then can help to supply information about the actual passivation. Especially, via the electrical contacting 80, 90 of the intermediate layers 20, 40 versatile information can be supplied both during production and during later operation of the implant. The reference numerals 110 and 120 in FIG. 2 denote, for example, switching devices (selector switches) for connecting a DC signal source 130 for measuring voltage and, resp., measuring current and a current measuring instrument 140 to respective components or layers of the multi-layer system each of which has to be activated.

Hereinafter, exemplary measurements on a passivating encapsulation of an implant will be described with reference to FIGS. 3 to 5, wherein the measurements shown in FIGS. 3 to 5 merely are for reference, as they were carried out against a reference electrode 100 located ex vivo outside an implant. However, it is noted that an implant located in vivo itself can supply equivalent information about the status of the passivation layers 10, 30, 50 based on the first and/or second intermediate layers 20, 40 made from conductive material as reference.

FIG. 3 schematically illustrates measuring signal sequences of simple electrical measurements on the implant of FIG. 1. The electrical measurements can be carried out, for example, at a voltage of 1 V by the reference electrode (PBS) 100 in the electrically active liquid against the two intermediate layers 20, 40 from conductive material as well as the electrode 60 of the implant. If no measurable current can be detected by the reference electrode 100 against the implant electrode 60, it can be concluded therefrom that the entire passivating system is still stable. FIG. 3 details on this basis that within the first 60 days following the beginning of the measurements no current is measurable between the reference 100 and the implant electrode 60 and the overall system thus is stably passivated. PBS stands for Phosphate Buffer Solution or Phosphate Buffered Saline, for example. PBS and the applicability thereof are known in so far and therefore will not be redundantly described here.

However, in practice the top passivating (polyimide) layer 10 can lose its passivating property after about 60 days in vivo, as shown in FIG. 3 by the measurably increasing currents after about 60.5 days. This loss of property and, resp., an increase in current caused in this way over a respectively observed measuring length (reference 100—passivation layer 10—upper intermediate layer 20, reference 100—central passivation layer 30—lower intermediate layer 40) then can be immediately measured via the upper first intermediate layer 20 (top layer) due to the electrical contacting 80 thereof. This is furthermore accompanied by a noteworthy immediate current detection on the lower second intermediate layer 40 (bottom layer). In this status, as shown in FIG. 3, still no current flow can be detected between the reference 100 and the implant electrode 60. This means that the overall system as such is still sufficiently passivated (via the bottom passivation layer 50), although the passivating effect of the passivation layers 10, 30 in the encapsulation is already measurably impaired. An increasing measuring current in FIG. 3 means a degradation of a respective passivation layer progressing over time (and possibly staggered in time between individual layers).

FIG. 4 illustrates a reference measurement from the liquid and, resp., from the reference electrode 100 to the upper first intermediate layer 20 as well as two electrical measurements exclusively within the implant, i.e. one measurement from the lower second intermediate layer 40 made from conductive material to the upper first intermediate layer 20 made from conductive material and one measurement from the lower second intermediate layer 40 to the implant electrode 60. Said measurements can equally be carried out by a DC signal and a voltage of e.g. 1 V.

As shown in FIG. 4, the implant (via the measurements within the implant) can itself detect degradation or deterioration of the central passivating (polyimide) layer, i.e. the second passivation layer 30 (lower curve in FIG. 4). Furthermore, it is evident from the measurement in FIG. 4 that the passivating multi-layer system is still stable as a whole despite the failure of two out of three layers (broken horizontal line in FIG. 4), as no measurable resistance is detected between the lower second intermediate layer 40 made from conductive material against the electrode 60.

It is possible to supply the above information about the functional state of the passivation solely by means of the implant without using any external reference and thus even after implantation of the implant in vivo. Accordingly, material fatigue can be detected early, while or although the passivating property is still given as a whole.

FIG. 5 exemplifies DC signal measurements via the first and second intermediate layers 20, 40. Such measurements can be used, for example, for detecting production reject.

FIG. 4 illustrates, by way of the occurrence of measurable currents, at the bottom left in the Figure the failure of the second passivating layer 30 simultaneously with the failure of the first passivating layer 10 after about 60.5 days. The measuring curves in FIG. 5 verify, however, that such simultaneous failure is not astounding and is predictable already on a predetermined day 0. For, although the overall system as such can be measured to be stably passivated (cf. the lower broken lines in FIG. 5 for measurements from the reference 100 against the intermediate layers 20, 40 and the electrode 60), according to FIG. 5 already initially a measurable current (and thus a detectable resistance) can be detected via the central passivation layer 30 by means of the first and second intermediate layers 20, 40 made from conductive material. The passivating property of said layer thus turns out to be not secured from the very beginning. This is then also confirmed (cf. FIG. 4) correspondingly in long-term measurement on the same object, preferably an implant, after about 60.5 days in this example.

FIG. 6 illustrates extracts from a simplified flow diagram of a method for determining the status of passivation layers according to one example embodiment on the basis of the afore-described measurements. In this example embodiment, an encapsulation of the implant by three passivation layers 10, 30, 50 and two intermediate layers 20, 40 is assumed. However, there is no restriction to any concrete shape and configuration of the encapsulation. For example, the number of the individual layers may be larger or smaller. It is further understood that technical means such as sensors, processing and control units, memories, interfaces and the like for carrying out the method are known per se, and therefore a description redundant in this respect may be omitted.

After the start of the method in a step S100, as afore-described, in a step S110 a DC signal is applied to components involved in a measurement to be carried out, for example via the DC signal source 130 and the switching devices 110, 120, and said components are switched to a detector, e.g. the current measuring device 140.

In a step S120 it is checked whether a current can be detected at the first and, resp., upper passivation layer 10, i.e. the passivation is impaired by said layer.

If no current can be detected and the passivation can be judged to be intact and, resp., stable by said layer (NO in step S120), the sequence progresses to a step S140.

If a current can be detected and the passivation must be judged to be degraded and, resp., deteriorated by said layer (YES in step S120), the sequence progresses to a step S130.

Alternatively, within the scope of an inspection of production reject, there may be a branching to a predetermined and suitable reject treatment (broken arrow line at step S120), if a corresponding criterion (e.g. "reject if top passivation layer 10 impaired") is applicable.

It is checked in step S130 whether at the second or central passivation layer 30 a current can be detected, i.e. the passivation is impaired by said layer.

If no current can be detected and the passivation by said layer can be judged to be intact and, resp., stable (NO in step S130), the sequence progresses to step S140.

If current can be detected and the passivation by said layer must be judged to be degraded and, resp., deteriorated (YES in step S130), the sequence progresses to step S140.

Alternatively, within the scope of an inspection of production reject, there may be a branching to a predetermined and suitable reject treatment (broken arrow line at step S130), if a corresponding criterion (for example "reject if top passivation layer 10 and central passivation layer 30 impaired") is applicable.

In step S140 it is checked whether at the third or lower passivation layer 50 a current can be detected, i.e. the passivation is impaired by said layer.

If no current can be detected and the passivation by said layer can be judged to be intact and, resp., stable (NO in step S140), the sequence progresses to step S160 in which the overall system can be judged to be stably passivated.

In step S160, then a reset of the sequence may be provided via which the determination of the status for an overall system judged to be stably passivated will be continued, until a predetermined degradation or impairment is detected which in a current processing cycle then branches to step 150 and further toward the end of the sequence for the currently considered overall system will branch in a step S170.

If a current can be detected and the passivation by said layer must be judged to be degraded and, resp., deteriorated (YES in step S140), the sequence progresses to step S150 in which the overall system is judged not to be stably passivated and thus to be functionally impaired. After that, processing for the currently considered overall system ends in step 170.

It is understood that the sequence shown in FIG. 6 is not restricted to the concrete sequence of the illustrated steps and that, in response to practical requirements, numerous modifications, combinations, supplements and omissions are possible.

For example, the flow diagram of FIG. 6 merely shows the measurement based on the reference electrode. However, it is understood that measurements can be carried out via the intermediate layers for detecting production reject or the quality of the individual layers by applying appropriate potentials to the intermediate layers, as afore-described, in a way equivalent and analogous to the measurements based on the reference electrode.

It is not absolutely necessary, for example, in response to applicable criteria that step S140 always has to be run, but for example already step S120 and/or step S140 may branch off to step S160, if a sufficient (stably intact) passivation by only one of the passivation layers 10, 30 suffices to judge the overall system as being stable.

Furthermore, an order of executing the steps to be individually carried out may be varied, for example if higher priority is attributed to an inspection of one of the passivation layers 10, 30, 50 than to that of other passivation layers.

In another modification, the order can be dynamically changed and/or shortened e.g. with progressing service life or, resp., useful life of the implant so as to increase a measuring frequency or to reduce the DC signal load of the overall system, for example when an expected value of the service life is approached. If e.g. the upper first passivation layer 10 and/or the central second passivation layer 30 is/are permanently detected to be degraded over a predetermined period of time, for example step S120 and/or step S130 can be suppressed and only step S140 can be checked for the remaining service life of the overall system.

It is understood that the invention is not limited to a concrete encapsulation and/or passivation structure on an implant but that various configurations and modifications are imaginable.

For example, the afore-exemplified measurements can be carried out in an application of a multi-layer passivation system to flexible substrates, for example a flexible electrically active polyimide substrate, for which information of the described type then can be supplied in vivo. The required electrical contacting of the intermediate layers 20, 40 can be made by means of ViaPads in the substrate 70 itself, for example.

Further, the afore-exemplified measurements can be carried out when applied to a flexible (not yet detached) substrate including multi-layer passivation. For example, in this case, by ViaPads at least two interposed layers made from conductive material, i.e. intermediate layers 20, 40, can be electrically contacted and can be read out along with further electrical components via BondPads, for example.

It is moreover understood that a merely exemplary nature is attributed to the described example embodiments and drawings which are not true to scale, and in so far modifications can easily result for those skilled in the art without departing from the scope according to the description. Equally, external shapes, dimensions and the like are not subjected to any special restrictions as long as the effect and the functionality according to the invention are provided and achieved thereby.

The invention claimed is:

1. A method for determining a status of an encapsulation and/or a passivation layer of the encapsulation, wherein the encapsulation forms a multi-layer system from multiple passivation layers arranged to lie alternatingly on top of one another, the multiple passivation layers comprising a top passivation layer and a bottom passivation layer, the top passivation layer forming a top layer of the multi-layer system and the bottom passivation layer forming a bottom layer of the multi-layer system, and electrically contacted intermediate layers arranged to lie between the passivation layers, the multi-layer system being arranged to protect an implant surrounded by the encapsulation, comprising the steps of:

carrying out an electrical measurement between a reference potential and at least one electrically contacted intermediate layer, and detecting at least one current flowing between the reference potential and the at least one electrically contacted intermediate layer; and comparing the at least one detected current with at least one pre-determined threshold value, wherein, if the at least one detected current falls below or exceeds the at least one pre-determined threshold value, this indicates a functional state of a passivation layer adjacent to the at least one electrically contacted intermediate layer, wherein the at least one pre-determined threshold value is zero and a comparison of detected measuring currents over plural layer sequences indicates a status of the entire multi-layer system forming the encapsulation, wherein if the multi-layer system includes at least one top, one central and one bottom passivation layer and if in an initial system inspection measurement after the end of production of the entire multi-layer system a measurable current is detected between a first intermediate layer interposed between the top and the central passivation layers and a second intermediate layer interposed between the central and the lower passivation layers via the central passivation layer, a basic impairment of at least the central passivation layer and/or of the entire multi-layer system which causes reject is concluded.

2. The method according to claim 1, wherein:

plural electrically contacted intermediate layers interposed between two respective passivation layers of the multiple passivation layers of the encapsulation are measured against a common reference potential, a respective measuring current is detected which is assigned to a corresponding one of the passivation layers and indicates the functional state thereof for each intermediate layer, and wherein each measuring current is compared to a respective pre-determined threshold value, wherein exceeding of the respective pre-determined threshold value indicates an impaired status of a respective assigned passivation layer.

3. The method according to claim 1, wherein the at least one pre-determined threshold value is zero and a comparison of detected measuring currents over plural layer sequences indicates a status of the multi-layer system, wherein, if the comparison indicates that at least between one electrode of the implant to be protected and an intermediate layer separated from the electrode by the bottom passivation layer no measuring current is detected, irrespective of a determined status of higher additional passivation layers a functional stability of the multi-layer system is concluded.

4. The method according to claim 1, wherein the encapsulation is arranged to encapsulate the implant, in vivo in a fluid-tight and/or gas-tight manner, and the method is configured to carry out, by way of analysis and evaluation of at least one passivating layer by electrical measurement, an in vivo failure analysis and/or health analysis of the implant passivation and/or detection of production reject while external reference components are omitted.

5. The method according to claim 1, wherein the electrical measurement is carried out between one electrically contacted intermediate layer and a second electrically contacted intermediate layer as the reference potential.

6. The method according to claim 1, wherein the electrical measurement is carried out on a biostable, biocompatible and electrically insulating encapsulation.

7. The method according to claim 1, wherein the method is carried out to pre-detect an impairment of passivating properties on a stably passivated multi-layer system.

8. A determining device configured and provided for determining a status of an encapsulation and/or of a passivation layer of the encapsulation, wherein the encapsulation forms a multi-layer system from multiple passivation layers arranged to lie alternatingly on top of one another, the multiple passivation layers comprising a top passivation layer and a bottom passivation layer, the top passivation layer forming a top layer of the multi-layer system and the bottom passivation layer forming a bottom layer of the multi-layer system, and electrically contacted intermediate layers arranged to lie between the passivation layers, the multi-layer system is arranged to protect an implant surrounded by the encapsulation, wherein the determining device comprises:

a measuring device configured and provided for carrying out electrical measurement between a reference potential and at least the electrically contacted intermediate layer of the encapsulation and for detecting at least one current flowing between the reference potential and the at least one electrically contacted intermediate layer; and a comparing device configured and provided for comparing the at least one detected current with at least one pre-determined threshold value, wherein, if the at least one detected current falls below or exceeds the at least one pre-determined threshold value, this indicates a functional state of a passivation layer adjacent to the at least one electrically contacted intermediate layer;

wherein the at least one pre-determined threshold value is zero and a comparison of detected measuring currents over plural layer sequences indicates a status of the entire multi-layer system forming the encapsulation, wherein if the multi-layer system includes at least one top, one central and one bottom passivation layer and if in an initial system inspection measurement after the end of production of the entire multi-layer system a measurable current is detected between a first intermediate layer interposed between the top and the central passivation layers and a second intermediate layer interposed between the central and the lower passivation layers via the central passivation layer, a basic impairment of at least the central passivation layer and/or of the entire multi-layer system which causes reject is concluded.

* * * * *